United States Patent [19]

Mignani et al.

[11] Patent Number: 5,535,048
[45] Date of Patent: *Jul. 9, 1996

[54] NONLINEARLY OPTICALLY ACTIVE COMPOUNDS

[75] Inventors: Gerard Mignani, Lyons; Gerard Soula, Meyzieu; Remi Meyrueix, Lyons, all of France

[73] Assignee: Flamel Technologies, Venissieux Cedex, France

[*] Notice: the term of this patent shall not extend beyond the expiration date of Pat. No. 5,359,072.

[21] Appl. No.: 210,995

[22] Filed: Mar. 21, 1994

Related U.S. Application Data

[62] Division of Ser. No. 714,585, Jun. 13, 1991, Pat. No. 5,359,072, which is a continuation of Ser. No. 407,744, Sep. 15, 1989, abandoned.

[30] Foreign Application Priority Data

Sep. 15, 1988 [FR] France .................................. 88/12028

[51] Int. Cl.$^6$ ............................. C07D 451/02; G02F 1/35
[52] U.S. Cl. ............................. 359/326; 252/582; 546/94; 548/566; 549/35; 558/426
[58] Field of Search ............................. 359/326; 385/122; 546/94; 548/566; 549/35; 558/426; 252/582

[56] References Cited

U.S. PATENT DOCUMENTS

| | | | |
|---|---|---|---|
| 5,053,168 | 10/1991 | Man et al. ......................... | 359/326 X |
| 5,359,072 | 10/1994 | Mignani et al. ..................... | 546/94 |

FOREIGN PATENT DOCUMENTS

| | | | |
|---|---|---|---|
| 2345189 | 1/1974 | Germany ............................. | 558/430 |
| 3214724 | 9/1988 | Japan ................................ | 548/570 |

OTHER PUBLICATIONS

Tripathy et al, *Chem. Tech., 1989*, pp. 747–752. *(No month)*.
Lemke, *Chem. Ber.*, 103, 1894–1899 (1970). (No Month).
Lemke, *Chem. Ber.*, 103, 3003–3006 (1970). (No Month).
Smith, *Optics* New York, J. Wiley & Sons), 1988, p. 266. (No Month).
Marder et al, "Approaches For Optimizing The First Electronic Hyperpolarizability Of Conjugated Organic Molecules," *Science*, vol. 252, Apr. 1991.
Cheng Et Al, "Experimental Investigations Of Organic Molecular Nonlinear . . . Derivatives," *J. Phys. Chem.*, vol. 95, No. 26, ACS, 1991. (No Month).
Singer Et Al, "Second Harmonic Generation In Poled Polymer Films", *Appl. Phys. Lett.*, vol. 49, No. 5, Aug. 1986.
Singer Et Al, "Second–Order Nonlinear–Optical Processes In . . . Properties," *Optical Society Of America*, vol. 4, No. 6, Jun. 1987.

*Primary Examiner*—John D. Lee
*Attorney, Agent, or Firm*—Burns, Doane, Swecker & Mathis

[57] ABSTRACT

Novel nonlinearly optically active compound's, well suited for electrooptical applications, have the following general formulae:

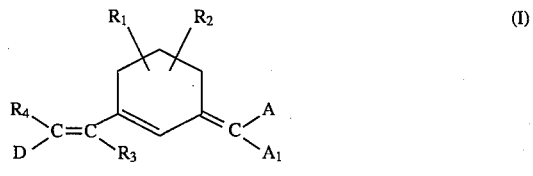

(I)

and

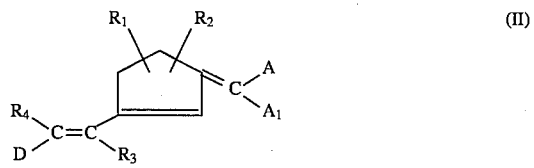

(II)

wherein D is an electron donor group; A and $A_1$, which may be identical or different, are each an electron acceptor group; and $R_1$, $R_2$, $R_3$ and $R_4$ are each a lower alkyl radical or a hydrogen atom.

21 Claims, No Drawings

NONLINEARLY OPTICALLY ACTIVE COMPOUNDS

This application is a divisional of application Ser. No. 07/714,585, filed Jun. 13, 1991, now U.S. Pat. No. 5,359,072, which is a continuation of application Ser. No. 07/407,744, filed Sep. 15, 1989, now abandoned.

BACKGROUND OF THE INVENTION

1. Field of the Invention

The present invention relates to novel organic compounds having nonlinear optical activity, and, more especially, to novel hyperpolarizable organic compounds well suited for inclusion in a matrix material to constitute a component of an electrooptical device.

2. Description of the Prior Art

As indicated by J. Zyszs and I. Ledoux, in an article published in *L'Echo des Recherches*, 1st trimester 1987, under the title "Organic Molecules and Treatment of Optical Signals", the future of optical telecommunications mandates the availability of components fabricated from materials having a strong nonlinear activity, on the second or third order.

Numerous compounds, both organic and inorganic, are used in different forms, such as solutions, liquid crystals, single-crystals, liquid polymer crystals, and the like.

Organic compounds are of great interest, as syntheses of a very wide variety of products, are typically enabled thereby. Furthermore, most organic compounds are highly resistant to deleterious external influences (humidity, acidity, oxidation, etc.) and may be incorporated in such materials as polymer films or the like.

J. F. Nicoud and R. J. Twieg, in their paper entitled "Design and Synthesis of Organic Molecular Compounds for Efficient Second Harmonic Generation", Ed. D. S. Chemla and J. Zyss (1987), report several molecules capable of nonlinear optical activity.

These molecules have carbon chain skeletons typically containing aromatic rings substituted, on the one hand, by electron donating groups and, on the other, by electron accepting groups.

The dislocation of electrons generates strong hyperpolarizabilities on the third and second order, when the molecule is noncentrosymmetric.

Large scale research efforts are continuously underway to discover and synthesize novel compounds having a nonlinear optical activity.

SUMMARY OF THE INVENTION

Accordingly, a major object of the present invention is the provision of a novel class of organic compounds having high nonlinear optical activity.

Briefly, the present invention features novel hyperpolarizable organic compounds having nonlinear optical activity and conforming to the following formulae:

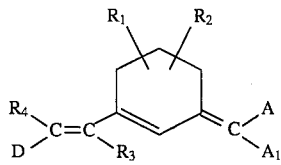

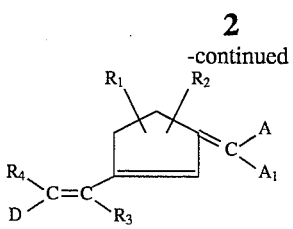

in which D is an electron donor group; A and $A_1$, which may be identical or different, are each an electron acceptor group; and $R_1$, $R_2$, $R_3$ and $R_4$ are each lower alkyl radicals or a hydrogen atom.

DETAILED DESCRIPTION OF THE PREFERRED EMBODIMENTS OF THE INVENTION

More particularly according to the present invention, the electron donor group D is advantageously a radical selected from among the following:

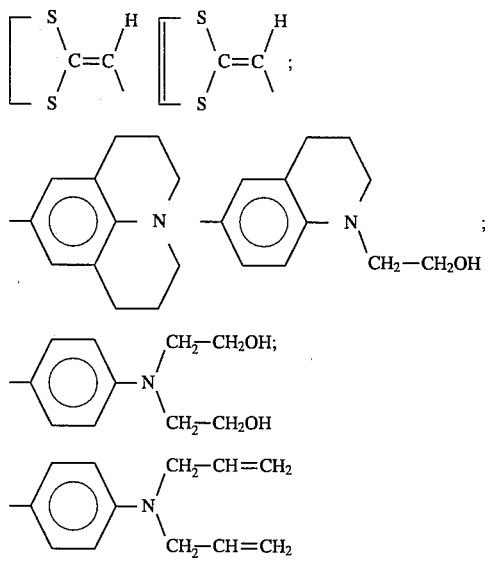

In another embodiment of the invention, the group D has the following general formula:

in which $R_6$ is an aryl radical, preferably benzylidene radical, and $D_1$ is an electron donating radical selected from among amino, alkylamino, dialkylamino, arylamino, hydroxyl, thiolo, alkylthio, arylthio, alkoxy, aryloxy, halogenoalkyl, oxy,

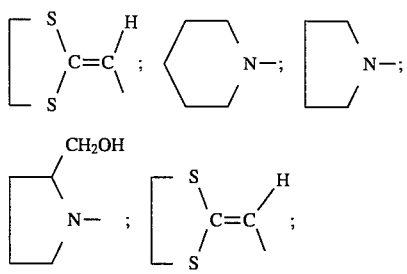

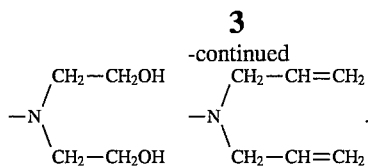

The preferred radical D of the invention is:

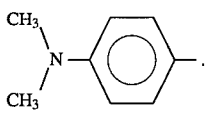

The A and $A_1$ groups, which may be identical or different, are advantageously hydrogen atoms or an electron acceptor radical selected from among nitro, cyano, —$CO_2R_5$ and —$PO_3(R_5)_2$ radicals, wherein $R_5$ is a lower alkyl radical, preferably ethyl or propyl.

Furthermore, the A and $A_1$ groups cannot simultaneously be hydrogen atoms.

The preferred radicals of the invention are the cyano and nitro radicals and, more particularly, the cyano/cyano and cyano/nitro combinations.

In a preferred embodiment of the invention, the novel compounds have a trans- configuration.

Particularly representative compounds according to the present invention have the following formulae:

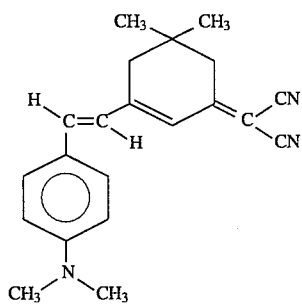
(A)

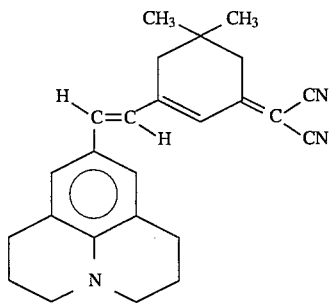
(B)

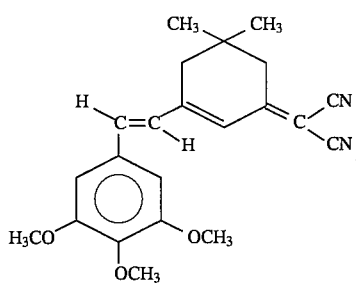
(C)

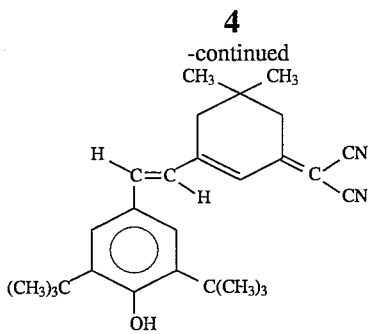
(D)

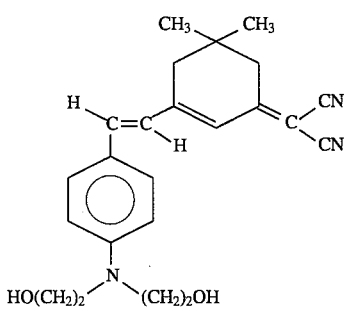
(E)

These compounds may be prepared by a number of different syntheses. Exemplary of such processes are those described in DE-2,345,189, in the article by Ralf Lemke, "Knoevenagel-Kondensationen in Dimethylformamid" (Knoevenagel condensations in dimethylformamide), published in *Synthesis*, 5, 359 (1974), or the article "Solvatochromie von 80 μm in verschiedmen Alkoholen bei Arylidenisophorm—Abkömmlignen", by the same author, published in *Chem. Ber.*, 103, 1894 (1970).

Briefly, such process entails carrying out the following reaction sequences:

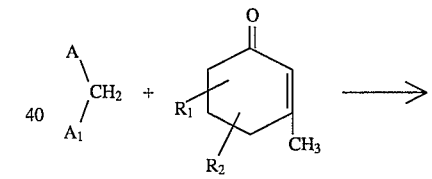

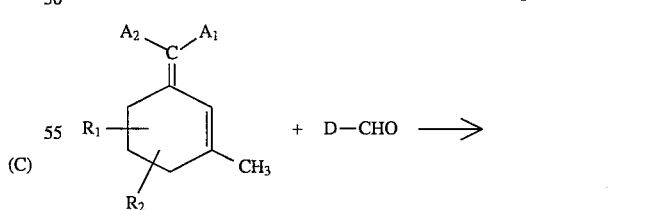

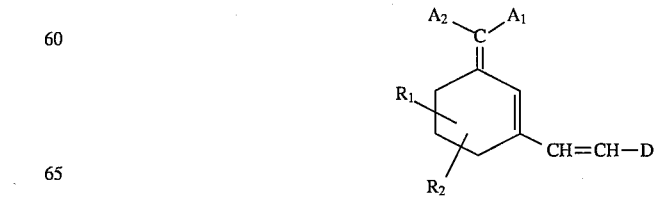

The latter condensation is known as the "Knoevenagel condensation".

The compounds of the invention display the important property of being optically active in nonlinear manner and, thus, well suited for incorporation in electronic or purely optical devices, in particular in the field of transducers, modulators, amplifiers, and the like.

In effect, the nonlinear optical activity is determined by the value of the coefficients β and γ of hyperpolarizability of the second, third or n order.

The hyperpolarizability of a compound is directly related to the dipolar molecular moment by the following fundamental relationship:

$$\mu = \mu o + \alpha \cdot E + \beta E . E + \gamma E . E . E . + \ldots$$

wherein μ and μo represent the dipolar moments, respectively, in the presence and absence of an electromagnetic field.

E represents the electrical or local electromagnetic excitation field.

α, β and γ represent the polarizability and hyperpolarizability coefficients.

Indeed, the α coefficient is the polarizability coefficient of the molecule and reflects its linear optical activity.

The β and γ coefficients represent the hyperpolarizability coefficients, respectively, of the second and third order.

These coefficients reflect the anharmonicity of the electric potential in the molecule and are strongly dependent on its symmetry and structure.

Furthermore, the coefficients of an odd order, such as the coefficient γ, are never zero for any molecule. In contrast, coefficients of an even order, such as the β coefficient, are zero for centrosymmetrical molecules.

It is advantageous to use molecules having a nonzero coefficient for nonlinear optical applications, such as, for example, electrooptical devices, electrooptical modulators, parametric amplifiers, frequency doubling devices.

To appreciate and measure the β coefficient of the molecules, it is determined by comparison with that of a reference molecule, i.e., urea.

The molecular hyperpolarizability β of a compound may generally be determined by an experiment for generating the second harmonic. It is carried out in a solvent medium such as, for example, acetone, water or dimethylsulfoxide. The method designated EFISH, is applicable and is described in the articles by B. S. Levine et al, *Appl. Phys. Lett.*, Vol. 24, p. 445 (1974) and J. L. Houdar et al, *J. Chem. Phys.*, Vol. 67, p. 1,926 (1977).

It is also possible to measure the product μβ (−w; w, O) by determining the electrooptical capability $X^{(2)}$ (−w; w, O) of doped and polarized PMMA film containing N active molecules per unit volume. $X^{(2)}$ (−w; w, O) may be measured by interferometry as described in the article by K. D. Singer et al, *J. Opt. Soc. Am.*, B, Vol. 4, No. 6, p. 968 et seq (1987). The relationship between μβ and $X^{(2)}$ is well known; it is described, for example, in the article by K. D. Singer et al, *Appl. Phys. Lett.*, Vol. 49, No. 5, p. 248 et seq (1986).

The hyperpolarizability of the molecule may also be determined by a static βμ coefficient, which corresponds to the activity of the molecule at zero frequency and which thus yields a measure of the intrinsic activity of the molecule.

For this, βμ is measured at a given frequency, for example by one of the aforementioned methods, and the value obtained reduced to a hypothetical zero frequency by means of a calculation designated the "two level model".

The method of calculating the static βμ is described in the article by K. D. Singer, published in *J. Opt. Soc. Am.*, B/Vol. 4, No. 6, p. 968 et seq (1987).

In order to further illustrate the present invention and the advantages thereof, the following specific examples are given, it being understood that same are intended only as illustrative and in nowise limitative.

EXAMPLE 1

Preparation of the Compound (A):

Into a flask, 10 ml piperidine and 600 ml ethanol were introduced as solvents, followed by 0.268 mole of

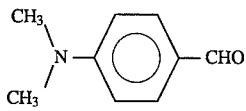

and 0.268 mole of

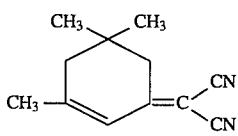

The mixture was maintained at reflux for 5 hours and then cooled to ambient temperature.

Compound (A) was recovered by filtration and washing with hexane.

The product collected was a red-violet solid having a melting point of 227° C.

NMR and mass spectrometry analyses confirmed the structure of Compound (A).

In addition, UV spectrometry analysis in a chloroform medium evidenced that the maximum wavelength (λ) of adsorption was 504 nm.

EXAMPLE 2

Preparation of the Compound (B):

To 100 ml ethanol, 0.268 mole of

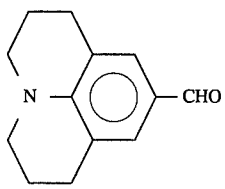

and 0.268 mole of

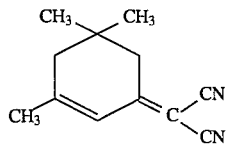

were added.

The mixture was heated to reflux for 48 hours and Compound (B) was permitted to crystallize at ambient temperature.

After filtration and washing with hexane, Compound (B) was recovered in the form of a violet solid with a melting point of 229° C.

NMR analysis, infrared and mass spectrography confirmed the structure of Compound (B).

The compound displayed, by UV spectrometry in a chloroform medium, a maximum adsorption wavelength of 550 nm.

EXAMPLE 3

Preparation of the Compound (C):

Following the procedure of Example 1, the compounds

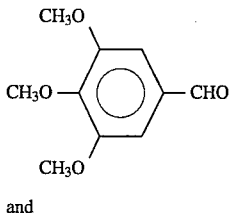

and

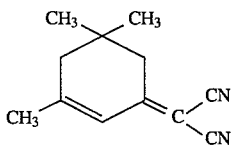

were reacted with each other.

Following crystallization, filtering and washing with hexane, an orange solid was recovered; it had a melting point of 211.5° C.

NMR analysis, IR and mass spectrometry confirmed the structure of Compound (C).

The maximum adsorption wavelength ($\lambda$ max) under UV spectrometry was 420 nm ($CHCl_3$).

EXAMPLE 4

Preparation of the Compound (D):

Following the procedure of Example 2, the following compounds were reacted with each other:

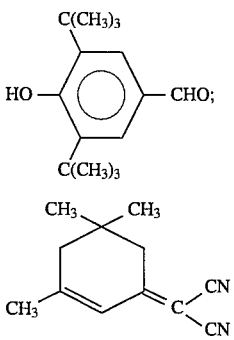

Following crystallization, filtering and washing with hexane, then recrystallization in a methanol/acetone mixture, a yellow-orange colored solid was recovered, having a melting point equal to 226.5° C. and $\lambda$ max of 437 nm ($CHCl_3$).

In a manner similar to the preceding examples, the various analyses confirmed the structure of the Compound (D).

EXAMPLE 5

Preparation of the Compound (E):

This compound was prepared by the reaction of the following compounds with each other:

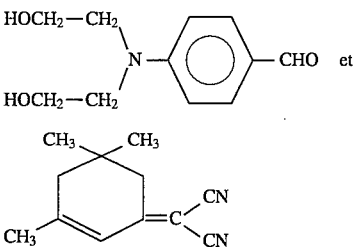

according to the procedure of Example 2.

The solvent was then evaporated to recover a red oil. Compound (E) was recovered by separation on a chromatographic column based on silica gel, with ethyl acetate as the eluant.

The product recovered was a red-violet solid having a melting point equal to 168° C. and having a $\lambda$ max of 494 nm ($CHCl_3$).

As in the preceding examples, the various analyses confirmed the structure of Compound (E) as shown above.

The results of the determination of the hyperpolarizability coefficient and the static coefficient of the different compounds are reported in the following table:

TABLE

| Example | Compound | Hyperpolarizability Coefficient $\beta\mu$ (-w; w; O) at $\lambda = 633$ nm | Static Coefficient $\beta\mu \times 10^{-48}$ e.s.u. |
|---|---|---|---|
| 1 | A | $11,710 \times 10^{-48}$ esu | 2,170 |
| 2 | B | $7,390 \times 10^{-48}$ esu | 750 |
| 3 | C | $880 \times 10^{-48}$ esu | 330 |
| 4 | D | $2,050 \times 10^{-48}$ esu | 710 |
| 5 | E | $10,610 \times 10^{-48}$ esu | 1,780 |

The compounds of the invention are incorporated in components of electrooptical devices in the form of materials, such as, for example, in the form of a film, by formulating same in a matrix, such as a polymer, a resin, etc., by conventional and known techniques.

Thus, for example, the compounds prepared according to Examples 1 to 5, were incorporated in a transparent polymer film of a thickness of 0.5 to 200 µm, as described in EP-218,938. Exemplary such polymers are, for example, polymethylmethacrylate and atactic polystyrene.

The polymer film was heated to a temperature higher than its glass transition temperature (Tg), then subjected to an intense electrical field to orient the active molecules according to the invention.

The film was then cooled to a temperature less than its glass transition temperature Tg, to freeze the active molecules in the oriented position.

A film containing the active oriented molecules of the invention had an electrooptical coefficient and a coefficient of generation of the second order harmonic comparable to those of the crystals customarily used for such applications, such as, for example, potassium diphthalate, ammonium diphthalate, potassium dihydrogenophthalate.

The film also provided specific advantages, such as a low dielectric constant and an electrooptical activity essentially of electronic origin.

The optoelectronically active materials, in particular in the form of films, are suitable for use in electrooptical modulators, active guides, such as directional couplers, polarizers, integrated modulators, and the like.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A hyperpolarizable organic compound displaying non-linear optical activity and having one of the following formulae:

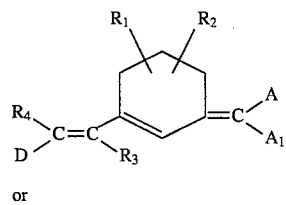

or

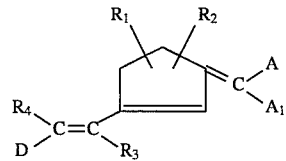

in which D is an electron donating group; A and A1, which may be identical or different, are each an electron accepting group; and $R_1$, $R_2$, $R_3$ and $R_4$ are each a lower alkyl radical or a hydrogen atom.

2. The compound as defined by claim 1, wherein D is one of the following radicals:

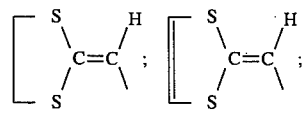

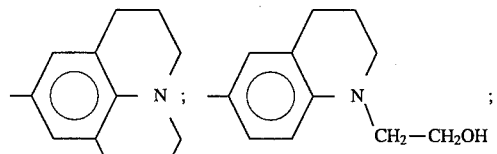

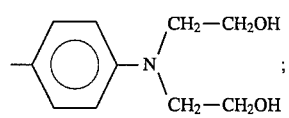

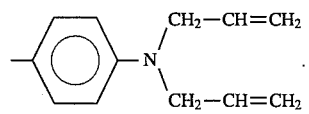

3. The compound as defined by claim 1, wherein D has the following formula:

in which $R_6$ is an aryl radical; and $D_1$ is one of the radicals: amino, alkylamino, dialkylamino, arylamino, hydroxyl, thiolo, alkylthio, aryloxy, halogenoalkyl, oxy,

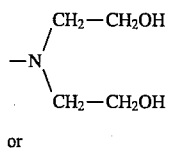

or

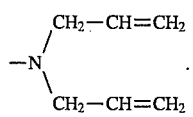

4. The compound as defined by claim 3, wherein $D_1$ is a dimethylamino radical.

5. The compound as defined by claim 1, wherein A and $A_1$, which may be identical or different, are each a hydrogen atom or a nitro, cyano, $-CO_2R_5$ or $-PO_3(R_5)_2$ radical, in which $R_5$ is a lower alkyl radical, with the proviso that A and $A_1$ cannot simultaneously each be a hydrogen atom.

6. The compound as defined by claim 5, wherein A and $A_1$ are cyano radicals.

7. The compound as defined by claim 5, wherein A and $A_1$ respectively are cyano and nitro radicals.

8. The compound as defined by claim 1, having a trans-configuration.

9. The compound as defined by claim 1, having one of the following formulae:

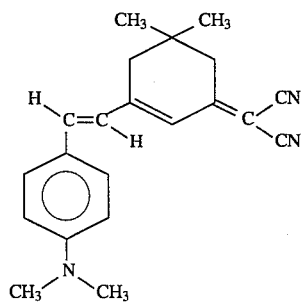

(A)

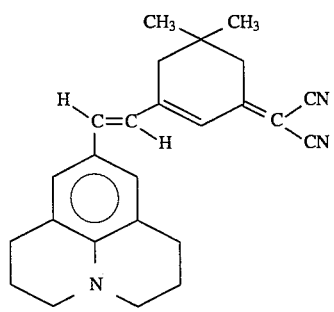

(B)

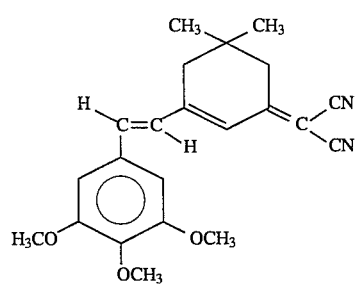

(C)

-continued

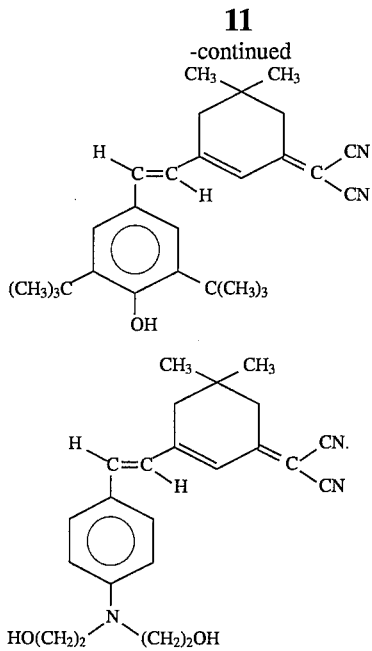

10. A nonlinearly optically active material comprising at least one compound as defined by claim 1.

11. The nonlinearly optically active material as defined by claim 10, capable of generating second order harmonics.

12. The nonlinearly optically active material as defined by claim 10, comprising a filled polymer film.

13. The nonlinearly optically active material as defined by claim 10, comprising an optoelectrical device.

14. The compound as defined by claim 1, having the formula (I).

15. The compound as defined by claim 1, having the formula (II).

16. In an electrooptical device including a matrix material comprising a nonlinearly optically active compound, the improvement which comprises, as said nonlinearly optically active compound therefor, a hyperpolarizable organic compound as defined by claim 1.

17. The electrooptical device as defined by claim 16, comprising a transducer, modulator, amplifier, directional coupler, polarizer, or frequency doubling device.

18. The electrooptical device as defined by claim 16, said matrix material comprising a transparent polymer film and said hyperpolarizable organic compound being electrical field-oriented therein.

19. In a matrix material component for an electrooptical device and comprising a nonlinearly optically active compound, the improvement which comprises, as said nonlinearly optically active compound therefor, a hyperpolarizable organic compound as defined by claim 1.

20. The matrix material component as defined by claim 19, comprising a transparent polymer film and said hyperpolarizable organic compound being electrical field-oriented therein.

21. The matrix material component as defined by claim 19, being in a form suitable for use in a transducer, modulator, amplifier, directional coupler, polarizer, or frequency doubling device.

* * * * *